United States Patent [19]

Biemann et al.

[11] Patent Number: 4,823,009

[45] Date of Patent: Apr. 18, 1989

[54] IR COMPATIBLE DEPOSITION SURFACE FOR LIQUID CHROMATOGRAPHY

[75] Inventors: Klaus Biemann, Alton Bay, N.H.; John J. Gagel, Cumberland Center, Me.

[73] Assignee: Massachusetts Institute of Technology, Cambridge, Mass.

[21] Appl. No.: 87,427

[22] Filed: Aug. 20, 1987

Related U.S. Application Data

[63] Continuation-in-part of Ser. No. 877,242, Jun. 23, 1986, which is a continuation-in-part of Ser. No. 851,445, Apr. 14, 1986.

[51] Int. Cl.[4] .................. G01N 21/01; G01N 1/28; G01N 1/10
[52] U.S. Cl. ............................. 250/341; 250/304; 250/339; 356/38; 422/70; 436/46
[58] Field of Search .................. 250/288 A, 304, 328, 250/341, 339; 356/38, 36, 244; 73/61.1 C; 210/659, 657; 436/46, 44, 161; 422/64, 66, 70

[56] References Cited

U.S. PATENT DOCUMENTS 3,496,102  2/1970  Dahl et al. .................... 210/358
3,924,947 12/1975  Hogg ............................. 356/39
4,552,723 11/1985  Adams et al. .................. 422/66

FOREIGN PATENT DOCUMENTS 79142  4/1986  Japan ............................. 250/339

OTHER PUBLICATIONS

Smith et al., "Deposition Method for Moving Ribbon Liquid Chromatograph-Mass Spectrometer Interfaces", *Anal. Chem*, vol. 53, pp. 739-740 (1981).
Harrick, *Internal Reflection Spectroscopy*, pp. 25-27 (1979).
Greenler, "Infrared Study of Adsorbed Molecules on Metal Surfaces by Reflection Techniques", Journal of Chem Phys. vol. 44, pp. 310-315 (Jan. 1966).

*Primary Examiner*—Janice A. Howell
*Assistant Examiner*—Constantine Hannaher
*Attorney, Agent, or Firm*—Fish & Richardson

[57] ABSTRACT

Effluent from a liquid chromatograph (LC) is deposited onto a deposition medium having a deposition surface inert to the LC effluent elevated above and parallel to a planar IR reflective front surface, preferably driven so as to define a continuous sample track in a generally circular, spiral or raster pattern. In the preferred embodiment, the deposition medium is a plate of germanium inert to aqueous and nonaqueous solvents, thicker than the longester IR wavelength of interest and having an undercoating of aluminum. Effluent is preferably deposited in a spiral pattern on the deposition medium in the form of a rotating disk. After collection, the reflection spectra can be interrogated by Fourier transform IR spectroscopy. The same collection technique can be used to collect and mount samples for mass spectrometry. To promote solvent evaporation, the effluent discharge is enveloped by a stream of heated nitrogen, particularly beneficial for reversed phase chromatography. By varying the temperature of the stream as a function of the proportions of solvents of differing volatility, the compatibility of gradient elution with surface deposition techniques is improved.

22 Claims, 8 Drawing Sheets

IR COMPATIBLE DEPOSITION SURFACE FOR LIQUID CHROMATOGRAPHY

The Government has rights in this invention pursuant to Grant Number NIH-5-P30-ES02109 and NIH-5-P01-ES01640 awarded by the Department of Health and Human Services.

CROSS REFERENCE TO RELATED APPLICATION

This application is a continuation-in part of application Ser. No. 877,242, filed June 23, 1986, by Klaus Biemann and John J. Gagel, which in turn is a continuation in part of application Ser. No. 851,445, filed Apr. 14, 1986, also by Klaus Biemann and John J. Gagel. Both applications are entitled "Method and Apparatus for Continuous Collection of Chromatographic Effluent", and are assigned to the assignee of the present application and incorporated herein by reference.

BACKGROUND OF THE INVENTION

The invention relates to liquid chromatography deposition media compatible with infrared (IR) analysis.

In the field of chemical analysis concerned with identification of organic compounds in complex mixtures, liquid chromatography is a widely used separation process which relies on the differential adsorption properties of organic molecules. Typically an organic mixture in a specific solvent is added to the top of a tubular column which has been packed with a fixed bed of adsorbent material providing surface area onto which substances may be adsorbed. As the solvent and solute mixture descend through the column, more strongly adsorbed compounds coat the packed bed surfaces, referred to as the stationary phase. The less strongly adsorbed substances, proceed through the column, along with the solvent. Ideally, the substances are progressively retarded into well separated segments. The eluted separated components of the mixture are discharged from the other end of the column along with solvent or eluent. Properly separated, the organic compounds come out of the column at intervals spaced by relatively pure solvent effluent.

For high performance liquid chromatography (HPLC), narrow columns known as microbore columns, may be employed to reduce solvent consumption and promote high solute concentrations. A commercially available microbore HPLC column 50 cm long with a 1 mm internal diameter is loaded with 10 micrometer ($\mu$m) silica beads. In normal phase chromatography, hydrocarbon solvents such as hexane and dichlormethane are used in the mobile phase. In reversed phase chromatography, polar organic solvents such as methanol are used in combination with water.

Once separated by chromatography, the individualized organic substances can be analyzed for identification by a variety of techniques, including, for example, IR spectroscopy, mass spectrometry, nuclear magnetic resonance, differential refractometry, heat of absorption detection and modified hydrogen flame ionization detection. In particular, the high scan speed and sensitivity of Fourier transform infrared (FTIR) spectroscopy has greatly facilitated the recording of characteristic infrared spectra of the individual components of mixtures separated by chromatographic techniques. Organic molecules in general contain interatomic bonds which exhibit characteristic vibrational frequencies, many of which happen to be in the mid IR region. These can be identified in the absorption spectrum of the material.

Interfacing HPLC with FTIR is hampered by infrared absorption of the extraneous solvent remaining in the mobile phase after separation. Two types of interfaces have appeared in the literature: (1) flow cells, which allow recording the IR spectra while the HPLC effluent flows by a window transparent in the infrared and (2) solvent deposition systems which involve transfer and elimination of the solvent on a medium compatible with infrared sampling.

In flow cells, the spectral contribution including spectral masking produced by the solvent material, which is still present at full strength, must be taken into account. Thus, analysis by the flow cell method is limited to solvents which happen to be transparent in wide regions of the infrared spectrum and even then, some areas of the spectrum will remain opaque resulting in loss of information and sensitivity.

Solvent deposition designs, on the other hand, involve depositing concentrated portions of HPLC effluent onto a collection medium and thoroughly evaporating the solvent. The deposits are then exposed to IR and the spectrum is measured and analyzed. Deposition surfaces thus offer the advantage of not only eliminating the solvent, but also leaving the solute on the collection surface as a record of the chromatographic separation. Collection media for analysis of deposits by transmission or reflection are limited to materials which do not have significant infrared absorbances of their own, the most practical such material being potassium bromide (KBr), which happens to be transparent over the entire intermediate infrared range examined in IR spectroscopy.

In general, the design of an interface for use with organic solvents common to normal phase HPLC has been possible since the solvents may be judiciously chosen to provide regions of IR transparency when used with flow cells, or can be evaporated during or after deposition on conventional infrared sampling media such as KBr. The use of aqueous solvents in the commonly employed reversed phase mode of HPLC, however, further complicates either design because water absorbs strongly over broad regions of the infrared, is of comparatively low volatility, thus frustrating evaporation, and readily dissolves KBr.

SUMMARY OF THE INVENTION

A general feature of the invention is an IR reflective deposition medium for LC effluent comprising an IR reflective planar front surface and a deposition surface elevated above the front surface and parallel thereto and substantially transparent over the IR range of interest for receiving and supporting effluent deposits for IR analysis. The height of the deposition surface above the front reflective surface is preferably greater than the longest quarter wavelength in the IR range of interest. The deposition surface is preferably formed by an IR transparent upper layer of a material inert to aqueous and nonaqueous solvents while the front reflective surface is provided by a layer of metal on the lower surface of the deposition medium. The upper layer is preferably a semiconductor material. Germanium offers certain advantages and zinc selenide is an alternative preferred material. The metal layer is preferably aluminum, copper or gold.

Another general feature of the invention is employment of the aforementioned deposition medium and apparatus for continuous collection and recording of components separated by liquid chromatography having an effluent discharge outlet, a plate having a planar IR reflective front surface and a substantially IR transparent deposition surface, preferably inert to aqueous and nonaqueous solvents, elevated above the planar front surface, and horizontally disposed beneath the discharge outlet with a drive mechanism to impart relative motion between the discharge outlet and the plate to define a continuous predetermined sample track on the deposition surface to form a deposit record of separated components for analysis by IR spectroscopy.

The preferred embodiments of the invention include providing the plate in the shape of a disk and imparting a generally circular motion thereto to define a spiral sample track. The foregoing apparatus is preferably combined with an IR spectroscopy system which directs an IR beam toward the deposits on the sample track while the plate is moved so that the beam traverses the sample track and an optical collector receives the IR which has been reflected from the planar surface after passing through the deposits for producing an output which is detected and analyzed to ascertain the R-A spectra.

Another general feature of the invention is a method of preparing a sample for spectroscopy by continuous collection of components separated by liquid chromatography in which the chromatographic effluent is deposited along a continuous predetermined sample track on an IR transparent deposition surface, preferably inert to aqueous and nonaqueous LC solvents, elevated above and parallel to a planar IR reflective surface. The sample track is preferably circular and preferably in the shape of a planar spiral.

Another general feature of the invention is preparing and analyzing continuously collected components separated by liquid chromatography in which effluent is deposited along a sample track on an IR transparent deposition surface, preferably inert to aqueous and nonaqueous solvents elevated above and parallel to a planar IR reflective surface after which an IR beam is directed toward the deposits along the sample track in accordance with a predetermined scan program for IR spectrographic analysis.

Another general feature of the invention is employment of the aforementioned deposition medium and apparatus for collection of components separated by liquid chromatography and sprayed onto the deposition surface by means of a nebulizer having a discharge outlet and a heating system for controllably heating the nebulized effluent as it is discharged from the outlet to promote solvent evaporation. Preferably, the amount of heating is varied as a function of the proportions of solvent components of differing volatility to accommodate respectively different heats of vaporization. This system is particularly useful in reversed phase chromatography. In the preferred embodiment, the apparatus includes means for enveloping the discharge nozzle in a stream of heated inert gas. This is preferably accomplished by means of a tubular shroud surrounding the nozzle supplied with heated inert gas such as nitrogen. In one embodiment, the tubular shroud includes an elongated bulb with a reduced inner diameter at one end substantially the same as the outer diameter of the portion of the nozzle which it engages while the forward end of the bulb has a cylindrical portion coaxially disposed around the forward portion of the nozzle and having an inner diameter substantially larger than the outer diameter of the adjacent surface of the forward end of the nozzle so that the rearward portion of the bulb centers the forward portion thereof with respect to the axis of the discharge nozzle.

The disclosed deposition medium allows continuous collection of effluent, compatible with reversed as well as normal phase chromatography and susceptible to IR analysis without distortion of the R-A spectrum.

DESCRIPTION OF THE PREFERRED EMBODIMENTS

We first briefly describe the drawings.

STRUCTURE OF COLLECTION/SPECTROSCOPY SYSTEM

The embodiments described herein are specifically designed to facilitate reflectance-absorbance (R-A) FTIR spectroscopy of compounds deposited from a microbore HPLC. The system is applicable, however, to other species of spectroscopy as well as spectrometry and may be extended to nonmicrobore forms of liquid chromatography presenting a liquid effluent. In particular, the present system is of the solvent deposition type rather than the flow cell type. The system can also be extended from HPLC to handle super critical fluid chromatography without major design changes. Both SCF chromatography and HPLC are intended to be embraced by the term "liquid chromatography" as used herein.

Figures 1, 2, 3:
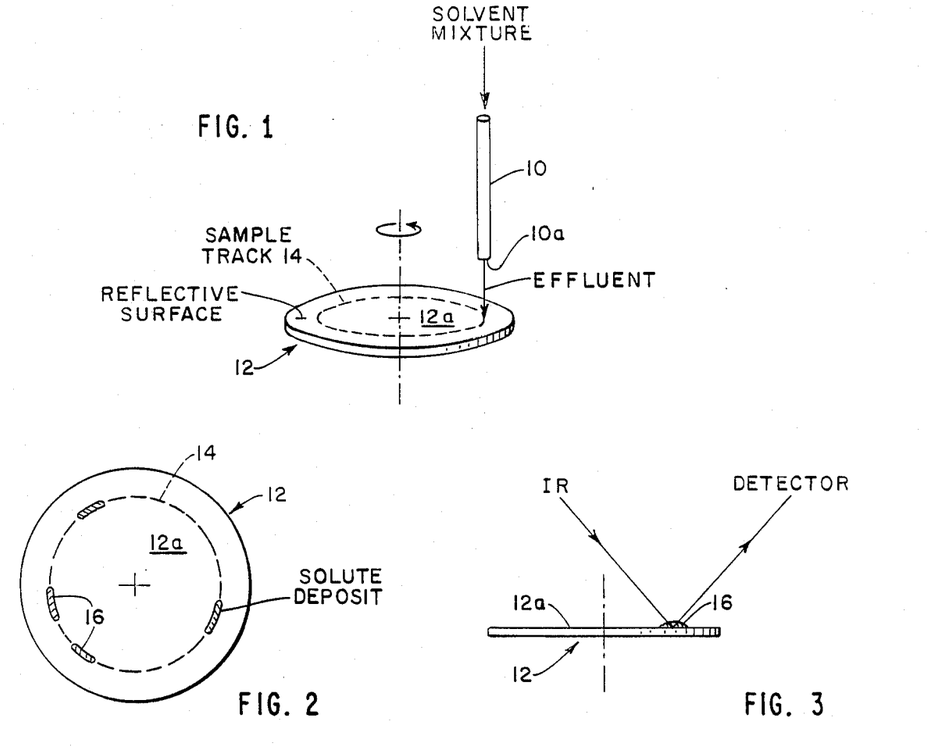
FIG. 1 is a perspective schematic representation of the continuous chromatographic effluent collection system according to the invention.
FIG. 2 is a plan view of the disk surface with a circular sample track.
FIG. 3 is a schematic side representation of the disk undergoing IR spectroscopy.

As shown in FIG. 1, effluent from a microbore HPLC column 10 having a discharge end 10a is deposited onto a circular disk 12 having a highly IR reflective front surface 12a which is impervious to common nonaqueous and aqueous solvents. The disk is arranged so that the reflective surface 12a is substantially horizontal to discourage running of the effluent deposit. The disk 12 is rotated about its axis as shown to define a circular sample track 14 for the effluent. As shown in FIG. 2, as the disk 12 rotates, effluent including any remaining solvent is deposited along the track 14. After the solvent evaporates, only the solute deposits 16 remain. If the solute has been properly separated, a series of spaced deposits are collected, as shown in FIG. 2. With a constant average rotation speed, the intervals between the solute deposits 16 correspond to the amount by which each successive component was chromatographically retarded. The surface 12a of the disk 12 allows for continuous collection of chromatographic effluent without limitation to particular solvents because the deposition surface 12a is inert to all common HPLC solvents.

After collection, the disk 12 is removed from the chromatographic apparatus and subjected to IR spectroscopy by training an IR beam on the solute deposits 16 along the sample track 14. The impinging IR beam is partially reflected after passing through the deposit 16 toward an IR detection system. The disk shaped mirror 12 may be rotated by a drive unit while spectra are recorded continuously. Alternatively, the disk can be rotated to a particular solute deposit and then stopped or reversed for repeated analysis of specific deposits.

Figure 4:
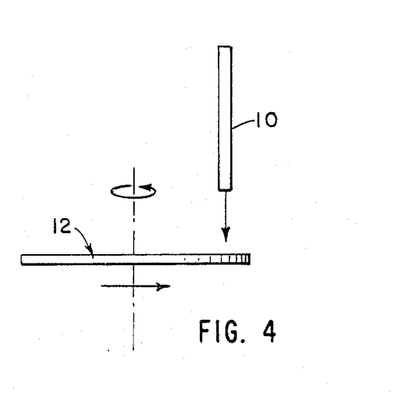
FIG. 4 is a schematic representation of the disk collection system of FIG. 1 with the drive mechanism modified to achieve a spiral track.
Figure 5:
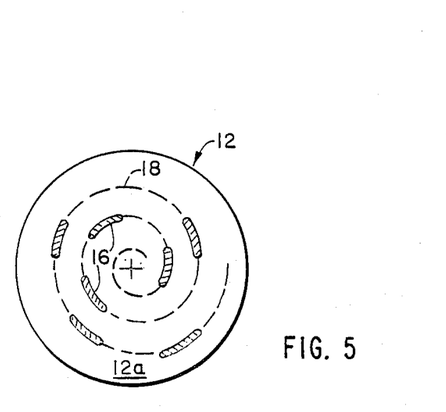
FIG. 5 is a plan view of the disk of FIG. 4 illustrating the spiral sample track.

As shown in FIGS. 4 and 5, the axis of rotation of the disk can be translated continuously or stepwise toward the effluent to achieve a long, continuous spiral sample track 18 as shown in FIG. 5. The spiral pattern expands the amount of chromatographic data obtainable with a single disk and thus may reduce its size.

Figure 6:
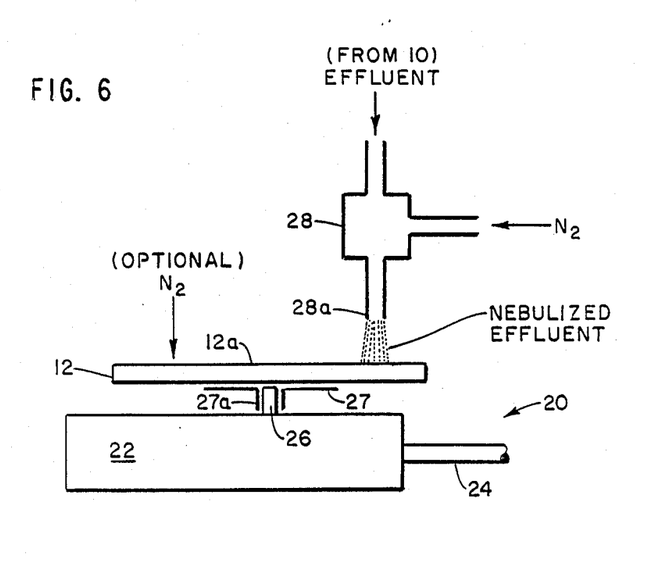
FIG. 6 is a schematic representation showing the disk viewed from the side in a preferred embodiment.

Experimental apparatus implementing the design of FIG. 1 is shown in FIG. 6. The disk 12 is mounted for rotation by a drive unit 20 including gear box 22 driven by a stepper motor through drive shaft 24. While a stepper motor does move stepwise or incrementally, the motion is referred to herein as substantially continuous for a series of rapid consecutive steps. Drive shaft 24 may be a removable or flexible shaft for ease of assembly and operation. The gear box 22 is machined from a block of aluminum and bored to provide space for right angle gears (not shown) to meet approximately 4 cm from its base. A vertical output shaft 26 extends above the gear box 22. The mirror attachment assembly is an aluminum disk 27 with three raised pods (not shown) on one side to which the underneath face of the disk 12 is epoxied. The attachment assembly 27 has a drilled central protrusion 27a which fits over the vertical shaft 26 on the gear box. The protrusion 27a has a tapped hole perpendicular to the shaft 26 which allows the assembly to be secured to the shaft by means of a set screw (not shown). With a stepper motor capable of 2,000 steps per revolution, each step corresponds to 0.08 mm for a typical sample track with a radius of 2.5 cm.

HPLC effluent is brought to a mixing Tee 28 from a conventional UV detector by a short length of stainless steel tubing (not shown). The outlet of the Tee is fastened to a syringe tip 28a. Fitting the syringe tip to the Tee port is accomplished by forcing Teflon tubing over the tip to give the proper external diameter and to make a gas tight liquid tight seal. The tip of the syringe is preferably held about 3 mm above the mirror surface 12a and results in a 1 to 2 mm wide solute deposit track. The other inlet to Tee 28 is connected to a source of pressurized nitrogen gas to nebulize the effluent. Nebulized effluent comes out of the syringe tip 28a just above the surface 12a of the collection disk 12. The nebulizer helps the solute dry faster and reduces residue on the syringe tip 28a. A gentle stream of nitrogen may be passed over the nebulized solvent after contacting the mirror surface 12a to rapidly evaporate any remaining solvents.

The discharge rate from a microbore column is typically 30 microliters per minute and chromatographic peaks are about 1 minute wide. Thus, rotational speeds of 4 mm/min measured along the sample track are used to provide a deposit length comparable to the beam width of the FTIR spectrometer.

Figure 7:
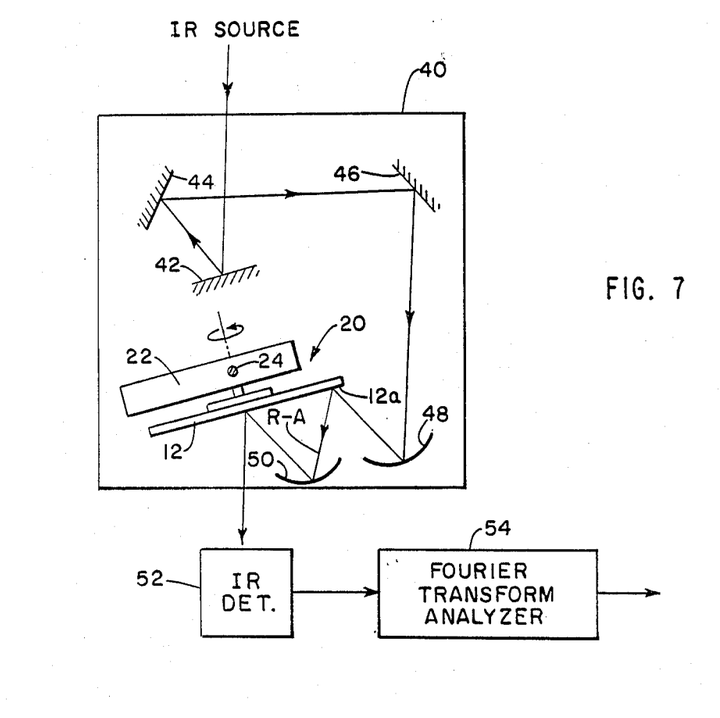
FIG. 7 is a plan schematic representation and block diagram illustrating the FTIR spectrographic apparatus with a reflectance accessory modified according to the invention.

After collection and evaporation of the solvent, the disk 12 is removed to a reflectance accessory 40 shown in FIG. 7 in a FTIR spectrometer, for example, a Digilab Model 15/90E. A prototype reflectance accessory was constructed from a Barnes Analytical Model 126 Reflectance Accessory modified by removal of the sample holder and a final plane mirror which directed the beam toward the detector. The drive unit 20 and mirror disk 12 are designed to take the place of these components. That is, the same mechanical apparatus shown in FIG. 6 (without the Tee, of course) is relocated following collection to the reflectance accessory 40.

A series of fixed plane mirrors 42, 44 and 46 directs the modulated infrared beam of a Fourier transform IR spectrometer. A concave focusing mirror 48 focuses the IR beam onto the sample track on the surface of the disk 12 for analysis of deposits. The R-A radiation reflected from the sample track is collected by concave front surface mirror 50 and redirected toward the center of the circular mirror 12 which reflects it onto an IR detector 52 whose output is fed to a Fourier Transform analyzer 54. In the Digilab Model 15/90E the detector 52 is a liquid-nitrogen-cooled wide band mercury/cadmium/telluride detector coupled with an interferometer operating at a moving mirror speed of 1.2 cm per second.

The 3-power beam condensing optics in the Barnes reflectance accessory aimed at a 20 degree incident angle to the disk 12 provided about a 2 mm spot size on the surface 12a with the spectrometer source aperture set to 6 mm. Under these conditions, the throughput of the reflectance unit with the device installed was just below the maximum dynamic range of the 15 bit analog-to-digital converter in the analyzer 54.

Operation of Collection/Spectroscopy System

In operation, utilizing the circular track system of FIGS. 1 and 2, effluent is collected at about 5 mm from the edge of the rotating mirror at a deposition speed of about 4 mm per minute. Under these conditions, a forty minute chromatographic run can be collected in a single track. FTIR spectroscopy allows continuously collected data to be obtained with software intended for GC/FTIR set to coadd eight scans at 8 cm$^{-1}$ resolution before transforming to form a scan set. This system provides a time resolution of 1.4 seconds. Gram-Schmidt chromatograms were calculated using reference vectors from a blank spot on the reflective surface or by reconstructing the data from interferograms taken during the run. The selection of coaddition regions for spectra of components from chromatographic runs was accomplished by using the automatic peak finding software available with the GC/FTIR software package. Wavelength chromatograms were created by Digilab supplied software which monitors absorbance at a user specified frequency throughout the chromatographic run or any portion thereof. For R-A spectra which shows excessive base line sloping or curvature due to scattering from the sample, a piecewise linear tracing of the base line can be generated using Digilab software. Subtraction from the raw spectrum provides a flatter base line and facilitates peak intensity comparison with standard spectra obtained using KBr powder. Sensitivity of the method according to the invention is increased by depositing the material over the smallest possible surface area and focusing the beam to a corresponding spot.

The ability to analyze the chromatographic run in a continuous fashion allows the use of the Gram-Schmidt reconstruction technique to indicate the presence of a deposited component and also the use of chromatograms to further interrogate the data for the presence of certain characteristic absorbance bands.

An important advantage of FTIR over conventional grating instruments is the ability to enhance spectral data by signal averaging many scans. The design of the preferred embodiment provides a record of the chromatographic separation which may be analyzed noncontinuously and may thus take advantage of these signal averaging capabilities. For continuous collection, lower resolution spectra are collected to increase time resolution and to save computer storage space. For noncontinuous analysis of selected components, there are no such concerns. The enhancement of minor separated components also can be accomplished in this way.

The design has other inherent advantages. During the collection step, the mirror speed may be reduced to enhance sensitivity by concentrating more material in a smaller track area or enhance the infrared chromatographic resolution by using a faster speed. With a computer controlled motor drive, the rotation of the mirror can be programmed to vary the speed during the chromatographic run to optimize resolution and sensitivity.

Although the present device could be developed for use on-line with the deposition step carried on inside the spectrometer, this would necessitate extracting solvent vapors which can interfere with the adsorption spectra. The time saved in the on-line experiment is small compared to the time required for sample preparations and analysis of the infrared data.

Deposition Media

Figure 8A:
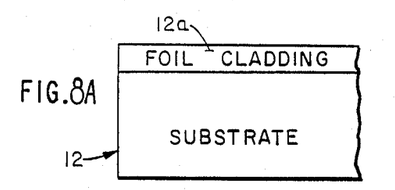
FIG. 8A is a sectional schematic view of the disk of FIG. 1 in the form of a foil clad substrate.
Figure 8B:
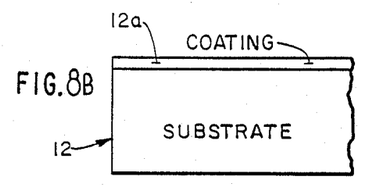
FIG. 8B is a sectional schematic representation of another embodiment of the disk of FIG. 1 in the form of a substrate with a deposited or plated coating.
Figure 8C:
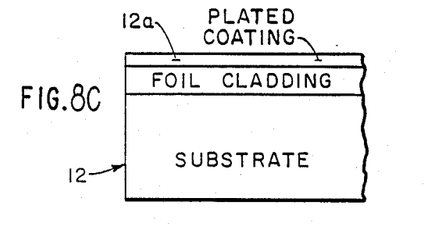
FIG. 8C is a sectional schematic representation of another embodiment of the disk of FIG. 1 in the form of a foil clad substrate with a plated coating over the foil.

FIGS. 8A, 8B and 8C illustrate three different techniques for preparing the disk 12. Foil cladding, deposited or plated coating or a combination of both, in which a plated coating is formed over the foil cladding, are all possible techniques. A smooth, flat reflective surface is important. A metal layer of aluminum, gold or copper can be deposited on glass, as in FIG. 8B, to produce a reflecting front surface.

Reflectance-absorbance spectra obtained from separated compounds using an aluminum front surface mirror as a deposition surface compare well to transmission spectra taken from KBr pellets. However, given sufficiently thin deposits, the use of a metal which is a good conductor, like aluminum, copper or gold, can introduce an artifact in the spectral distribution. In particular, it has been discovered that when an aluminum front surface mirror is used to collect thin deposits, the spectrum is significantly skewed or biased toward high frequency (i.e., short wavelength) absorptions. The suppression of low frequency (long wavelength) absorptions can be explained by realizing that a standing wave with a node at the metal surface is created by superposition of the incident and reflected wave when a conductor is used as the reflector at near normal incidence. Thus, right at the metal surface, the magnitude of the electric vector component of light is zero and no interaction with the sample may take place. Proceeding upward from the surface, the electric vector of the standing wave increases to a maximum located a quarter wavelength above the surface. Accordingly, the maximum will be closer to the surface for short wavelengths than for long wavelengths. For a thin deposit, the average sample height may be significantly less than a quarter of the longest wavelength of interest. Thus, a sufficiently thin deposit will be exposed to a stronger electric vector at shorter wavelengths allowing for greater absorbance. This effect causes both a reduction in sensitivity and a loss of sample information at long wavelengths when small amounts of material are to be analyzed. Absorbance bands at these long wavelengths are of particular importance in the spectra of substituted aromatic compounds since the analysis of peaks in this region can differentiate substitutional isomers—a well known feature of IR spectroscopy which is not possible by other analytical methods such as mass spectrometry.

Figure 9:
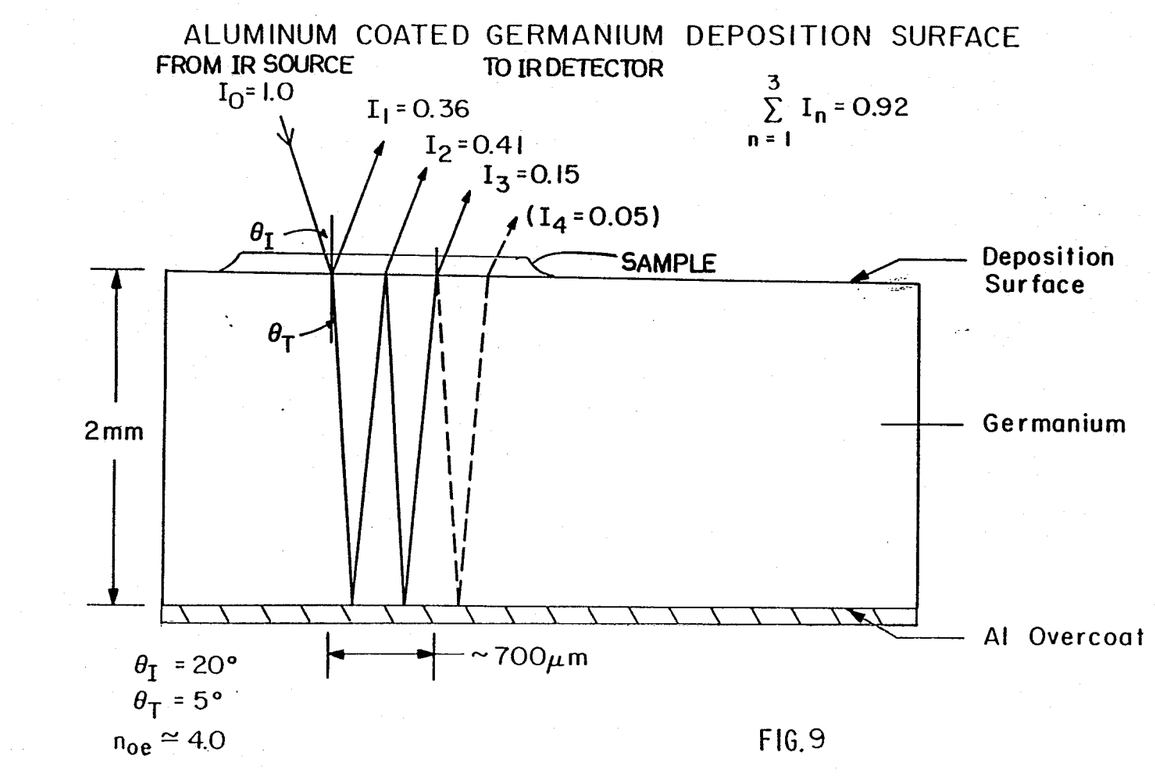
FIG. 9 is a sectional schematic representation of a composite deposition medium.

It has been discovered that the deposition medium may be designed specifically to avoid a standing wave node at the deposition surface. In particular, as shown in FIG. 9, a germanium crystal thicker than the longest infrared wavelengths of interest is coated on one side with a highly infrared reflective material such as aluminum. The effluent from a HPLC is deposited onto the germanium surface and the solvent is evaporated. The deposition medium bearing the sample deposits is then placed in a reflectance accessory such as that of FIG. 7 and exposed to an infrared beam. As shown in FIG. 9, the beam passes through the sample to the germanium surface. Germanium, as it turns out, has a very high refractive index (about 4, compared to 1.5 for KBr) and is also highly and uniformly transparent to intermediate IR wavelengths. Consequently, at the surface, the beam $I_0$ is partially transmitted and partially reflected as shown. The reflected component $I_1$ passes back through the sample and is directed onto the detector (or collection mirror 50 of FIG. 7). The transmitted component is refracted closer to normal ($\theta_t$) and, passes through the germanium to the aluminum interface at which point it is fully reflected back toward the front surface of the germanium through the sample and on to the detector as $I_2$. The reflected beam travelling back up through the germanium is partially transmitted and partially reflected at the interface with the sample. The relative intensities (absent a sample) for four outgoing beams $I_1$–$I_4$ derived from a single incident beam $I_0$ are shown in FIG. 9. The first three outbound beams have collectively over 90% of the incident intensity. Thus, R-A throughput is comparable to a highly reflective metal and far better than an uncoated Ge crystal. Proper selection of the angle of incidence and germanium thickness minimizes multiple internal reflections. For example, in a collection disk with a 60 mm diameter, the germanium layer had a thickness of 2 mm, as shown in FIG. 9, and the angle of IR beam incidence, $\theta_I$, was 20°, with 12° being about the minimum practical angle. The thickness of the aluminum layer is unimportant.

Germanium forms a good deposition surface since it is inert to common normal and reversed phase solvents. Germanium has the added advantage of being resistant to acid modified solvent.

Instead of germanium, other materials highly transparent to IR can be employed keeping in mind that they should be nonsoluble in common HPLC reversed phase solvents as well as normal phase solvents. Zinc selenide is an alternative material. However, if there are acids in the effluent, they will react with it to produce hydrogen selenide. Gallium arsenide is not as transparent over the whole intermediate range but might be satisfactory in certain applications.

The absorbance intensity bias due to standing wave effects in a metal front surface reflector are markedly reduced in the structure of FIG. 9 in two different ways. First, the reflected component shows less intensity bias since the electric field vector of a reflected wave is appreciably greater than zero for a semiconductor like germanium at near normal incidence. Secondly, the light passing through the germanium front surface and rebounding off the aluminium coating passes through the deposit in a transmission mode. The germanium thickness thus constitutes a means of elevating the deposition surface above the IR reflective front surface o the aluminum layer to displace the deposit from the standing wave node at the aluminum surface. In this position, the deposit, no matter how thin, should be seated at least as high as the longest quarter wavelength of interest where the first electric vector maxima occurs for the standing wave at the metal surface. Preferably, the displacement is many times the quarter wavelength distance to avoid thin film interference effects. The germanium thus acts as an IR transparent buffer layer, as well as a reflector. With heights of several millimeters (e.g., 2 mm), the precise thickness of the layer becomes noncritical and close tolerances need not be observed.

Figure 10:
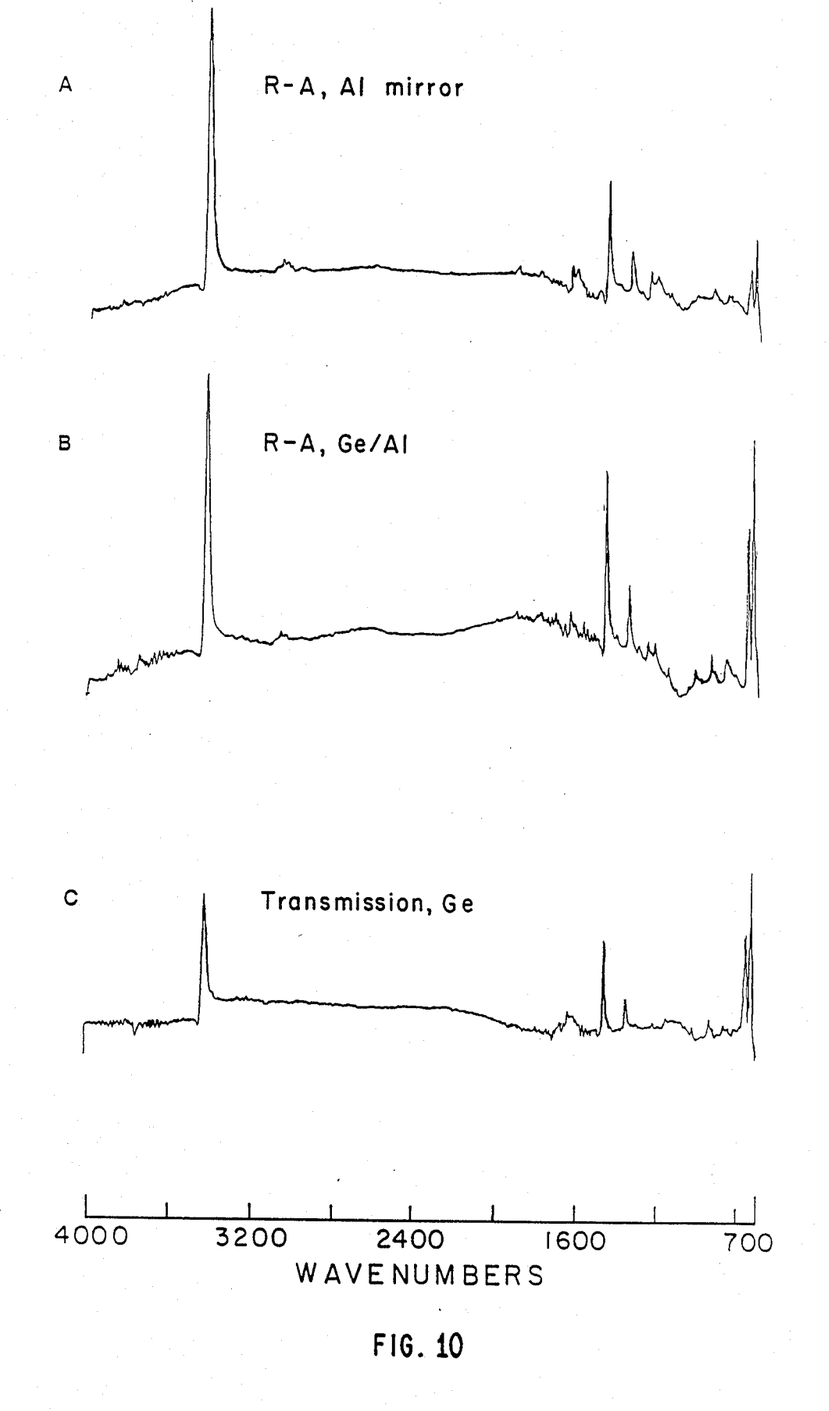
FIG. 10 is a composite graph of the R-A spectra of samples of carbazole on two different deposition media A and B, and of the transmission spectra C.

FIG. 10 illustrates the R-A spectra of a thin sample of carbazole hand spotted onto aluminum (wave form A) and a germanium/aluminum surface like that of FIG. 9 (wave form B) are compared with spectra of the same compound taken in the transmission mode through an uncoated germanium crystal (waveform C). All three spectra are plotted on the same scale. The relative absorbance of bands in the region below 800 cm$^{-1}$ (wave number) in the aluminum deposit spectrum (A) compared to the germanium/aluminum data (B) illustrates the effect of displacing the standing wave node at the surface; indeed, the sub-800 spectra is comparable to the pure transmission experiment (C). The germanium/aluminum type configuration should therefore allow lower detection limits for sample deposition by HPLC/IR and allow greater spectral information to be obtained at long infrared wavelengths for small amounts of deposited material. Furthermore, analysis of deposits in the R-A mode with this device results in a factor of two pathlength advantage over a simple transmission measurement on Ge since the beam is reflected back through the sample from the aluminum coated underside. In FIG. 10, the R-A spectra show higher absorbance intensity than the transmission spectrum even at short wavelengths because of this effect.

Figure 11:
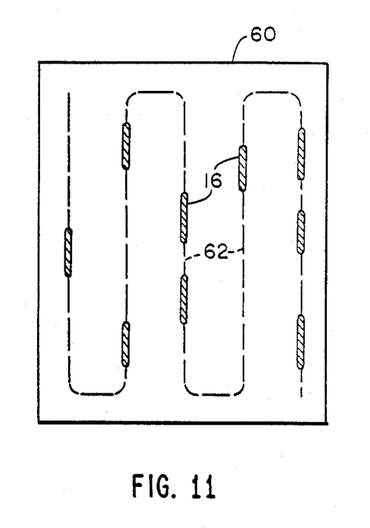
FIG. 11 is a plan schematic representation of another embodiment of the collection plate in rectangular form with a sample track in a raster pattern.

FIG. 11 shows another embodiment of the collection plate which instead of being in the form of a disk 12 is in the form of a rectangular plate 60. In this design, the drive unit (not shown) is modified to execute a raster scan pattern for the sample track 62. Solute deposits 16 are left on the surface 60a along the raster track.

Mass Spectrometry Application

Figure 12:
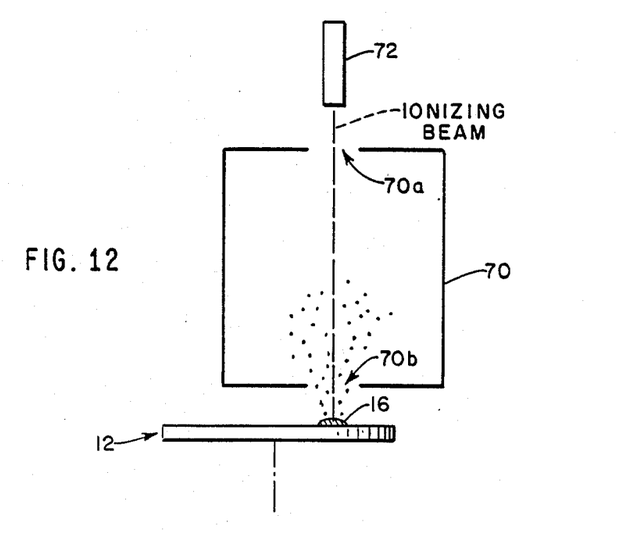
FIG. 12 is a schematic representation illustrating a chromatographic collection disk undergoing mass spectrometry according to the invention.

Mass spectrometry provides another possible means of identification of components separated by liquid chromatography. The collection system of the present invention is not only compatible with but also advantageous for all forms of mass spectrometry, including Fourier transform, magnetic deflection, time-of-flight and quadrapole spectrometry. A Fourier transform mass spectrometer is diagrammed in FIG. 12. An ionizing cell 70 having means for producing electrical and magnetic fields (not shown) has aligned ports 70a and 70b to allow a beam of ionizing radiation to pass through the cell to the sample located beneath port 70b. The sample to be ionized is carried on the collection disk 12 or rectangular plate 60 (FIG. 11) on which deposits 16 have been continuously collected during chromatography. The disk 12 and ionizing trapping cell 70 are in a vacuum chamber (not shown). A beam of ionizing radiation, for example, from a high power laser 72, impinges on the deposit 16 generating ions of the sample material which are drawn through the opening 70b into the trapping cell 70. For mass spectrometry, an IR reflective surface on the disk 12 is unnecessary although acceptable. Indeed, following chromatographic collection, the same disk 12 could be subjected sequentially to IR spectroscopy and then mass spectrometry to obtain comparative spectra for verification or further analysis.

For time-of-flight mass spectrometry with $^{252}$CF desorption, the samples are preferably carried on a thin foil surface. The foil clad disk construction illustrated in FIG. 8A can be used in collection and, after removal of the substrate, the deposits would be on a medium compatible with spectroscopic analysis.

Structure of Effluent Discharge System

Figure 13:
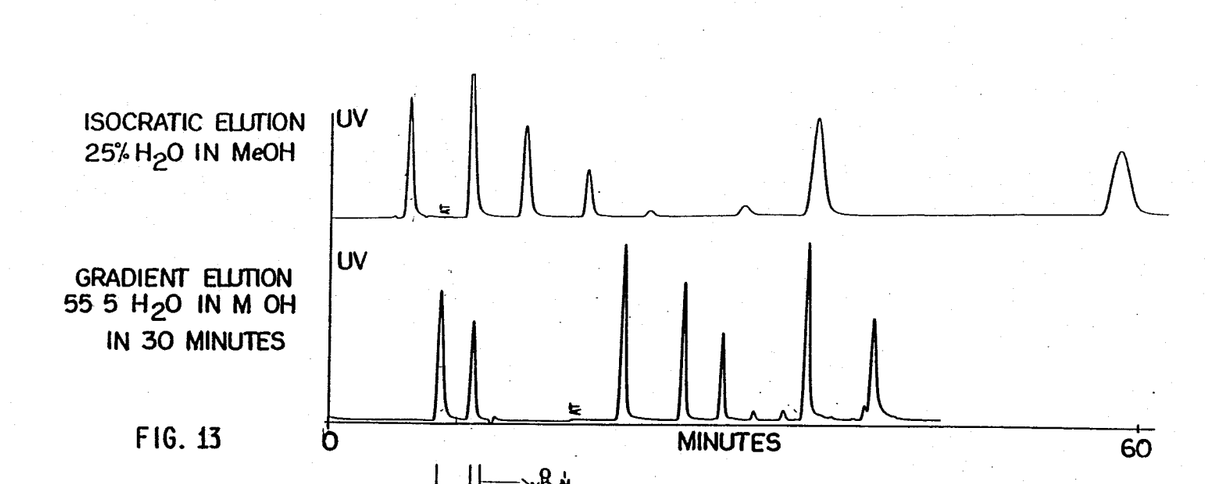
FIG. 13 is a composite graph of UV absorbance versus time for an isocratic elution and a gradient elution of the same test mixture.
Figure 14:
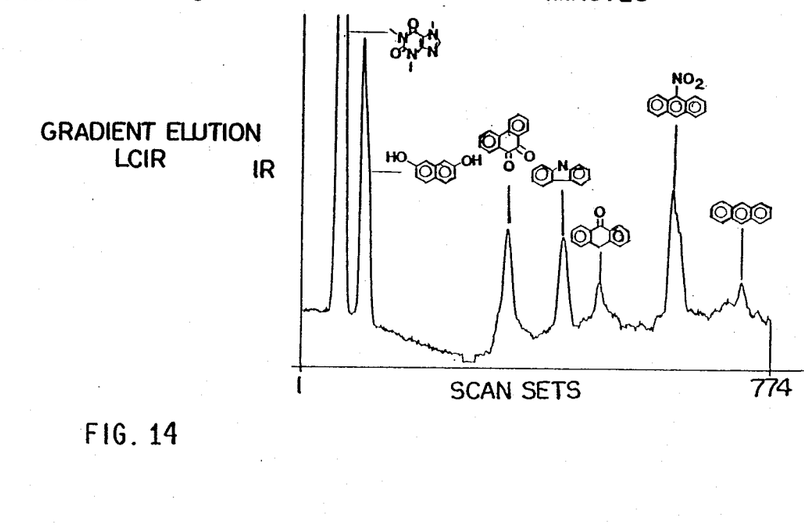
FIG. 14 is an infrared (Gram-Schmidt) chromatogram prepared from the gradient elution of FIG. 13.

FIGS. 13-18 illustrate a variation on the effluent discharge system for the collection apparatus of FIG. 6, which promotes uniform deposition in HPLC, particularly reversed phase, where less volatile aqueous solvents are harder to eliminate. The objective is to evaporate as much of the solvent as rapidly as possible as the effluent (mist, FIG. 6) emerges from the nebulizer and hits the deposition surface. If solvent elimination is too slow, it wets the deposition surface and tends to spread the solute out or run, thereby decreasing the concentration of solute under the IR beam and degrading the chromatographic resolution in the subsequent analysis.

The system of FIG. 15 is specifically designed to heat the discharged stream as a function of the concentration of aqueous solvents which require more heat for evaporation. In gradient elution, two or more solvents or elutants are mixed and fed to the column in continuously varying proportions. For example, in a water and methanol combination, the volume of water might begin at about one half and decrease to nil in one run. In the graphs of FIG. 13, UV detection demonstrates the advantage of gradient elution over isocratic (constant proportions) elution. The mixture undergoing analysis contains seven organic compounds. However, reversed phase chromatography with 25% water in methanol yields only six UV peaks (upper graph) and requires 60 minutes for elution of the final component. With gradient elution, the proportion of water declining from 55% to 5%, another peak is uncovered (the second peak from the left in the lower graph), all of the peaks are sharpened and the duration of the run is substantially shortened. FIG. 14 shows the results of FTIR spectroscopy on the deposits from the same gradient elution as in the lower graph of FIG. 13, using the deposition technique according to the invention with a complementary heating gradient in the discharge stream.

These results are made possible by bathing the nebulizer tee syringe tip 28a in a coaxial stream of heated nitrogen flowing in the same direction as the effluent.

Figure 15:
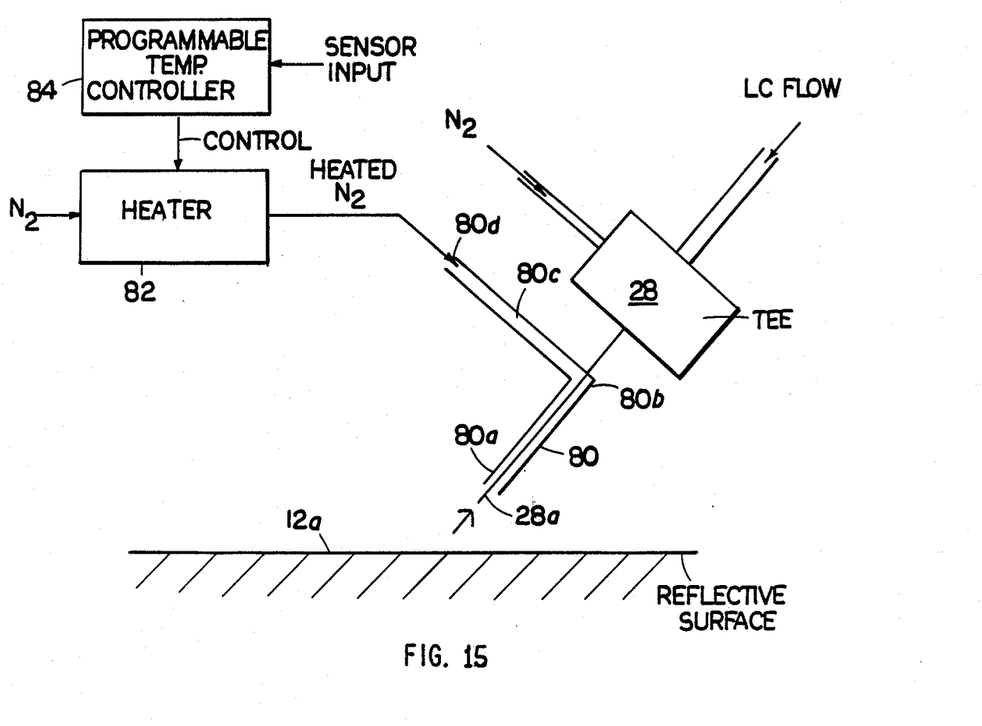
FIG. 15 is a block and schematic diagram of a nebulized effluent heating system according to the invention.

As shown in FIG. 15, tubing 80 is fitted coaxially over the nebulizer outlet, i.e., the hollow syringe tip or needle 28a. The inner diameter ("ID") of the tubing 80 adjacent the needle 28a is considerably larger than the outer diameter ("OD") of the needle to define a generally cylindrical space between the needle and tubing. The forward end 80a of the tubing 80 is open except for the protruding tip of the needle 28a and the rearward end of the tubing 80 is sealed to the needle. The tubing 80 has a side arm 80c with an inlet 80d.

A stream of pressurized nitrogen ($N_2$), which may be provided by the same source which supplies the nebulizer 28, is fed through heater 82 to the inlet 80d of the tubing 80. Heater 82 is regulated by a programmable temperature controller 84.

Operation of Effluent Discharge System

In operation, the heated nitrogen stream blows over the end section of the nebulizer needle 28a covered by the tubing 80 and out the end 80a of the tubing. The exiting nitrogen stream entrains the mist discharged from the nebulizer needle tip 28a. The heated external nitrogen stream functions to heat the liquid inside the needle 28a by heating the needle itself. In addition, the heated nitrogen stream blowing out of the end of the tubing 80 heats the discharge from the end of the needle 28a by impinging directly on the mist. Further, the nitrogen stream blowing along the tip of the needle 28a acts as an auxiliary atomizer to help form the spray better. The nitrogen stream creates additional turbulence so as to break up larger droplets discharged or clinging to the end of the syringe tip 28a.

Tubing 80 with side arm 80c can be formed of a continuous length of Teflon ® tubing into which the needle 28a is inserted in the manner of an intravenous catheter. The punctured end 80b can be sealed by heating the tubing sufficiently to melt it and bond it sealingly to the needle where the needle passes through the wall of the tubing. The diameter of the tubing can be necked down at the forward end 80a to achieve a desired ID, for example, twice the OD of the needle.

Figure 16:
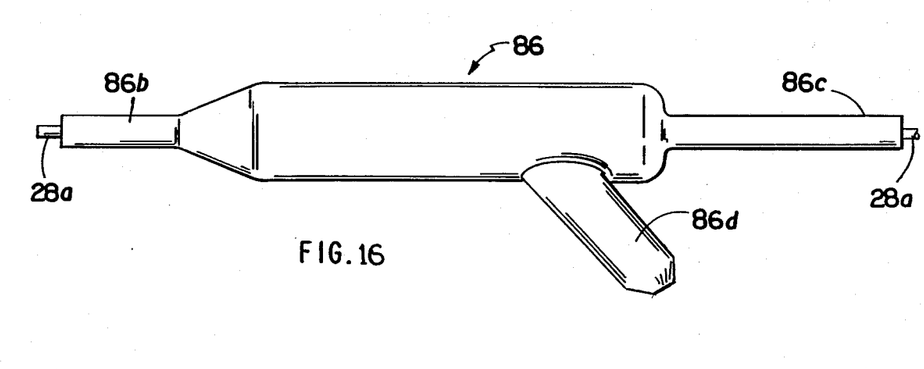
FIG. 16 is a side view of a shroud-like bulb enveloping the nebulizer needle.
Figure 17:
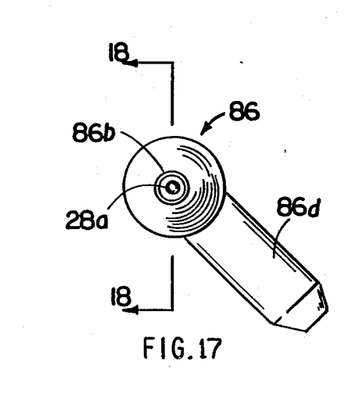
FIG. 17 is a front view of the bulb of FIG. 16.
Figure 18:
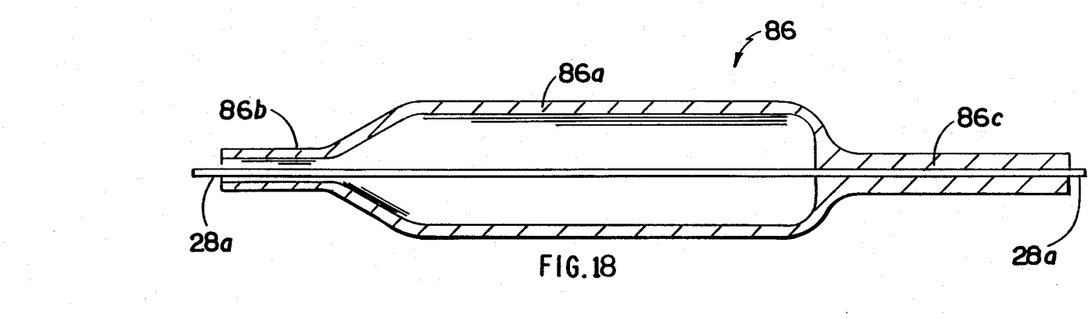
FIG. 18 is a sectional view of the bulb taken along the lines 18—18 of FIG. 17.

Another embodiment of the tubing 80 is shown in FIGS. 16–18. A glass bulb 86 includes an elongated cylindrical body 86a, a forward nozzle end 86b of reduced diameter, a rearward stem portion 86c of reduced diameter and an integral side arm 86d (FIGS. 16 and 17). The stem portion 86c has an ID which is as close as possible to the OD of the needle 28a while the nozzle end 86b has an ID exceeding the OD of the needle by a predetermined margin to define the annular exit cross-section for the nitrogen stream. In practice, with a needle of 0.64 mm OD, the ID of the nozzle 86b may be approximately 1 mm. The axes of the nozzle and stem ends are aligned so that when the needle is inserted through the bulb 86, the stem end centers the nozzle end 86b around the needle 28a. Bulb 86 may be made of glass, a thermoset or thermoplastic material or a machined metal, if desired. Flexible tubing connected to the nitrogen heater 82 is fitted over the end of the side arm 86d.

Heater 82 and controller 84 (FIG. 15) can be implemented in several different ways. For example, copper tubing carrying the nitrogen stream can be coiled tightly around a cylindrical heater block having resistive heating coils embedded in a ceramic material. A constant level of electrical current to the resistive heating coils can be switched ON and OFF by a simple thermostatic control element having a thermocouple, corresponding to the sensor input in FIG. 15, connected to the outer wall of the copper tubing along the heating block. Instead of using the tubing as the heat exchanger, the resistive heating elements can be placed directly inside the nitrogen duct for direct heating. In this alternative, an enlarged plenum segment is equipped with inner heating elements like a hair dryer. Similarly, a thermocouple for thermostatic control can be located downstream of the inner heating coils to sense temperature of the nitrogen stream.

Whether the resistive heating elements are inside or outside the duct, the electrical current can be controlled if desired by making the current level a function of the error signal between the set point (desired temperature) and temperature sensor output. Another possibility would be to sense the amount of liquid on the disk directly using a laser beam and regulate temperature to maintain a minimum level.

In normal phase chromatography, the nebulizer usually sufficiently evaporates the solvent. The temperature of the auxiliary nitrogen stream exiting around the syringe tip may, however, be maintained advantageously at a constant level slightly above room temperature.

It is in reversed phase chromatography where the less volatile solvents require substantial additional heating to evaporate them sufficiently for good deposition. There are constraints on the temperature of the auxiliary nitrogen stream. Too little heat and the solvent-containing effluent puddles on the deposition surface. Too much heat and the solvent completely evaporates before discharge thus allowing a residue to plate out on the inside of the needle 28a.

For gradient elution, the temperature of the auxiliary nitrogen stream is continuously adjusted as a function of the proportions of aqueous and nonaqueous solvents. For the example given in FIG. 13 (lower graph), the temperature of the nitrogen stream is continuously lowered from 78° C. at 55% water to 45° C. at 5% water. The ideal relationship between temperature and water proportions is assumed to be approximately linear. Because heat transfer is a function of flow rate as well as temperature, and the action of the exiting auxiliary stream on the discharged effluent should not be varied, the flow rate of the nitrogen stream should be maintained as constant as possible. For this purpose, a plenum capable of careful pressure regulation in the nitrogen line would probably be desirable.

The reflective continuous collection plate technique represents a novel approach which eliminates the problems associated with solvent absorbance in flow cell designs and reduces the inherent complexity of previous solvent deposition techniques while providing complete continuous collection and analysis on a surface impervious to aqueous as well as nonaqueous solvents. The system used in HPLC is capable of sensitivity in the nanogram range. The sample plates are compact, inexpensive to manufacture and reusable. Depending on the length of the continuous track and angular velocity of the disk, several runs can be recorded on the same disk. The disks are compatible with all types of spectroscopy and mass spectrometry. Rotational speed can be programmed to tailor the deposition area or to maximize resolution of closely eluting compounds. The design of the system allows many scans of many samples to be easily taken and stored for computation. A variety of scan programs can be accommodated—from a continuous survey scan along the entire track to a detailed examination of a single deposit with the disk held stationary. In the latter mode, the signal to noise ratio of weak absorbances can be enhanced by signal averaging many scans. The intervals between deposits can be examined as a time record of separation intervals. Identification markings can be easily added to the disks to catalog the relatively permanent physical record in which the order of components for each entire chromatographic run is preserved. A portable drive unit system allows the same mechanism to be employed for collection and spectroscopy at different locations insuring that the sample track is followed accurately during off-line spectroscopy or mass spectrometry.

Deposition of effluent in reversed phase liquid chromatography is enhanced by a heated auxiliary nitrogen stream surrounding the discharge end of the nebulizer. This improvement aids in evaporation and improves the spray pattern to make more compact, more concentrated, solvent-free deposits of solute on the deposition surface. The auxiliary heated stream technique is applicable to normal phase chromatography, and could even be used with those methods utilizing KBr deposition surfaces. However, even greater advantages are realized in reversed phase chromatography. Because the degree of evaporation can be closely controlled by modulating the auxiliary stream temperature with a simple resistive heating element, the temperature can be tailored for gradient elution so that the amount of solvent left in the spray does not fluctuate. The resulting deposits can be obtained more quickly and yield sharper results than isocratic elution using the same solvent system on the same test mixture.

Finally, the use of deposition media having an inert IR transparent buffer layer above the fully IR reflective layer exhibits more uniform absorption spectra at the longer IR wavelengths. The elevated deposition surface design is useful by itself as a collection media for IR sampling, but has added utility in combination with the other disclosed features of applicants' collection/spectroscopy system and effluent discharge system.

The foregoing description is intended to be only illustrative of several forms in which the invention may be implemented. Any number of other variations and modifications are possible without departing from the principle of the invention. For example, the HPLC system can be modified to accommodate super critical fluid chromatography. Other shapes of the collection plate or sample track are possible besides those shown herein and other means of imparting relative motion between the nebulizer and the reflective surface area, of course, possible without affecting the principle of operation. The scope of the invention is indicated, of course, by the appended claims and equivalents thereto.

We claim:

1. A deposition medium for collecting LC effluent for analysis over a range of IR wavelengths, comprising
    an IR reflective planar front surface, and
    a deposition surface inert to the LC effluent positioned above said front surface a distance greater than the longest quarter wavelength in said range, parallel thereto and substantially transparent over said IR range for collecting effluent deposits for IR analysis.

2. A deposition medium for collecting LC effluent for analysis at a range of IR wavelengths, comprising
    an IR transparent upper layer inert to the LC effluent having an exposed upper deposition surface, and
    a layer of IR reflective metal on the lower surface of said medium such that IR passing through said upper layer is reflected back through said upper layer by the front surface of said metal layer, said upper layer being thicker than the longest quarter wavelength in said range.

3. A deposition medium for collecting LC effluent for analysis at a range of IR wavelengths, comprising
    an IR transparent upper layer inert to the LC effluent having an exposed upper deposition surface, and
    a layer of IR reflective metal on the lower surface of said medium such that IR passing through said upper layer is reflected back through said upper layer by the front surface of said metal layer, said upper layer being made of a semiconductor material.

4. A deposition medium for collecting LC effluent for analysis at a range of IR wavelengths, comprising
    an IR transparent upper layer inert to the LC effluent having an exposed upper deposition surface, and
    a layer of IR reflective metal on the lower surface of said medium such that IR passing through said upper layer is reflected back through said upper layer by the front surface of said metal layer, said upper layer being on the order of 1 mm thick.

5. A deposition medium for collecting LC effluent for analysis at a range of IR wavelengths, comprising
    an IR transparent upper layer inert to the LC effluent having an exposed upper deposition surface, and
    a layer of IR reflective metal on the lower surface of said medium such that IR passing through said upper layer is reflected back through said upper layer by the front surface of said metal layer, said upper layer being made of germanium.

6. A deposition medium for collecting LC effluent for analysis at a range of IR wavelengths, comprising
    an IR transparent upper layer inert to the LC effluent having an exposed upper deposition surface, and
    a layer of IR reflective metal on the lower surface of said medium,
    such that IR passing through said upper layer is reflected back through said upper layer by the front surface of said metal layer, said upper layer being zinc selenide.

7. The medium of claim 5, wherein the thickness of said upper layer is on the order of 1 mm.

8. The medium of any of claims 2-7 wherein said metal layer is made of a metal selected from the group consisting of aluminum, copper and gold.

9. Apparatus for continuous collection and recording of LC effluent components, comprising
   an outlet for discharging effluent from a liquid chromatograph,
   a plate having a planar IR reflective front surface and a substantially IR transparent deposition surface inert to the LC effluent elevated above said planar front surface and parallel thereto,
   a plate mounting support oriented so that said deposition surface is horizontally disposed beneath said outlet, and
   a drive mechanism imparting relative motion between said outlet and said plate to define a continuous predetermined sample track on the deposition surface of said plate such that effluent is deposited on the deposition surface to form a record of separated components along a continuous sample track for analysis by IR spectroscopy, said plate including a germanium layer providing said deposition surface.

10. The apparatus of claim 9, wherein said germanium layer is thicker than the longest quarter wavelength of interest in said range.

11. The apparatus of claim 9, further comprising an off-line IR spectroscopy system including
   an optical system arranged to direct an IR beam toward an area of incidence on said predetermined sample track,
   a drive mechanism imparting relative motion between said beam and said plate so that the area of incidence of said beam is movable along said predetermined sample track,
   an optical collector to receive IR reflected from said area of incidence for producing an output,
   a detector connected to receive the output of said collector for detecting the varying level of IR reflection along said sample track and for producing an output indicative thereof, and
   an analyzer responsive to the output of said detector means for producing an output indicative of the IR spectra along said sample track,
   said collector including a concave mirror which redirects IR toward a portion of said deposition surface away from said sample track so that it is reflected from said plate toward said detector.

12. Apparatus for collection of LC effluent components, comprising
   a medium having a planar IR reflective front surface and an IR transparent deposition surface inert to the LC effluents elevated above and parallel to said IR reflective front surface,
   a nebulizer for nebulizing the effluent from the column,
   an outlet for discharging nebulized effluent toward said deposition surface, and
   a heating system for controllably heating the nebulized effluent as it is discharged from said outlet means to promote solvent evaporation, said heating system including
   a controller to vary the amount of heating of said discharged effluent in relation to the proportions of solvent components of differing volatility to accommodate respectively differing heats of vaporization.

13. Apparatus for collection of LC effluent components, comprising
   a medium having a planar IR reflective front surface and an IR transparent deposition surface inert to the LC effluents elevated above and parallel to said IR reflective front surface,
   a nebulizer for nebulizing the effluent from the column,
   an outlet for discharging nebulized effluent toward said deposition surface, and
   a heating system for controllably heating the nebulized effluent as it is discharged from said outlet means to promote solvent evaporation,
   said outlet including a nozzle, and said nebulizer including means for mixing the effluent from the column with a pressurized inert gas and passing the mixture through the nozzle.

14. The apparatus of claim 13, wherein said heating system includes means for enveloping said nozzle in a stream of heated inert gas.

15. The apparatus of claim 14, wherein said heating system, includes a controller to vary the temperature of the inert gas stream as a function of the proportions of solvent components of differing volatility to accommodate respectively differing heats of vaporization.

16. The apparatus of claim 13, wherein said heating system includes means for enveloping said nozzle in a substantially coaxial stream of heated inert gas flowing in the same direction as the effluent.

17. The apparatus of claim 16, wherein said enveloping means includes a tubular shroud surrounding said nozzle, and means for supplying said heated inert gas to the interior space between said shroud and said nozzle.

18. The apparatus cf claim 17, wherein the rearward end of said shroud is sealably connected with respect to said nozzle and the forward end of said shroud is substantially open to permit the outflow of inert gas to envelop the discharge end of said nozzle.

19. The apparatus of claim 18, wherein said forward end of said shroud is generally cylindrical and coaxial with said nozzle so as to form therewith a substantially annular opening.

20. The apparatus of claim 19, wherein the discharge end of said nozzle protrudes from the forward end of said shroud.

21. The apparatus of claim 20, wherein said tubular shroud includes an elongated bulb having a cylindrical rearward end coaxially mounted over said nozzle and having an ID substantially the same as the OD of a portion of said nozzle on which said rearward end is received, the forward end of said bulb having a cylindrical portion coaxially disposed around a forward portion of said nozzle and having an ID substantially larger than the OD of the adjacent surface of said nozzle, and port means defined in the side wall of said bulb for admitting heated inert gas, such that said rearward portion of said bulb centers the forward portion thereof with respect to the axis of said nozzle.

22. The apparatus of claim 21, wherein said nozzle is in the form of a hollow needle.

* * * * *